US006232511B1

(12) United States Patent
Haas et al.

(10) Patent No.: US 6,232,511 B1
(45) Date of Patent: May 15, 2001

(54) PROCESS FOR THE PRODUCTION OF 1,3-PROPANEDIOL BY HYDROGENATING 3-HYDROXYPROPIONALDEHYDE

(75) Inventors: Thomas Haas, Frankfurt; Dahai Yu, Bad Orb; Jorg Sauer, Rodenbach, all of (DE); Dietrich Arntz, Mobile, AL (US); Andreas Freund, Kleinostheim; Thomas Tacke, Friedrichsdorf, both of (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/424,979

(22) PCT Filed: Jun. 16, 1998

(86) PCT No.: PCT/US98/12584

§ 371 Date: Dec. 2, 1999

§ 102(e) Date: Dec. 2, 1999

(87) PCT Pub. No.: WO98/57913

PCT Pub. Date: Dec. 23, 1998

Related U.S. Application Data

(60) Provisional application No. 60/058,509, filed on Sep. 11, 1997, and provisional application No. 60/056,505, filed on Aug. 21, 1997.

(30) Foreign Application Priority Data

Jun. 18, 1997 (DE) .............................................. 197 25 753

Aug. 27, 1997 (DE) .............................................. 197 37 190

(51) Int. Cl.$^7$ ....................................................... C07C 29/41
(52) U.S. Cl. ................................................................ 568/862
(58) Field of Search .............................................. 568/862

(56) References Cited

U.S. PATENT DOCUMENTS

| 2,434,110 | * | 1/1948 | Hatch et al. ......................... 260/602 |
| 5,334,778 | * | 8/1994 | Haas et al. ........................... 568/862 |
| 5,874,652 | * | 2/1999 | Pitchai et al. ........................ 568/862 |

FOREIGN PATENT DOCUMENTS

| 3926136 | * | 2/1991 | (DE) . |
| 0343475 | * | 11/1989 | (EP) . |
| 0535565 | * | 7/1993 | (EP) . |

* cited by examiner

Primary Examiner—Peter O'Sullivan

(57) ABSTRACT

A process for the production of 1,3-propanediol by heterogeneously catalyzed hydrogenation of 3-hydroxypropionaldehyde in an aqueous solution at 30 to 180° C., at a hydrogenation pressure of 5 to 300 bar and a pH value of 2.5 to 7.0, wherein ruthenium on an oxide support is used as the catalyst.

10 Claims, No Drawings

PROCESS FOR THE PRODUCTION OF 1,3-PROPANEDIOL BY HYDROGENATING 3-HYDROXYPROPIONALDEHYDE

This application is a 371 of PCT/US98/12584 filed Jun. 16, 1998 and relies on its priority of provisional application 60/056,505 and 60/058,509 filed Aug. 21, 1997 and Sep. 11, 1997 respectively.

FIELD OF THE INVENTION

This invention relates to a process for the production of 1,3-propanediol by hydrogenating 3-hydroxypropionaldehyde.

BACKGROUND OF THE INVENTION 1,3-Propanediol is used as a monomer unit for polyesters and polyurethanes and as a starting material for synthesizing cyclic compounds.

Various processes are known for the production of 1,3-propanediol which start either from $C_2$ and $C_1$ structural units or from a $C_3$ structural unit, such as, for example, acrolein. When acrolein is used, this compound is first hydrated in the presence of an acidic catalyst, wherein 3-hydroxypropionaldehyde (3-hydroxypropanal) is formed. Once the unreacted acrolein has been separated, the aqueous reaction mixture formed during hydration still contains, in addition to 85% 3-hydroxypropionaldehyde, approximately 8% oxaheptanediol and further organic components in smaller proportions by weight. This reaction mixture is hydrogenated in the presence of hydrogenation catalysts to produce 1,3-propanediol.

According to Hatch et al. U.S. Pat. No. 2,434,110, catalysts suitable for hydrogenating 3-hydroxypropionaldehyde are those containing one or more metals having a hydrogenating action, such as, for example, Fe, Co, Cu, Ag, Mo, V, Zr, Ti, Th, and Ta. Raney nickel and Adkins' copper/chromium oxide may also be used as catalysts.

According to Arntz et al. DE-PS 39 26 136, the catalyst may be used either in suspended form or supported or as a constituent of fixed bed catalysts; homogeneous catalysts may also be used. Suspended catalysts which are mentioned are Raney nickel, which may be doped with various other catalytically active metals, and plantinum on activated carbon.

Prior art catalytic hydrogenation entails the risk that small quantities of the catalytically active element will be discharged into the product stream in the form of soluble compounds, making necessary further steps to separate the resultant contaminants. This may in particular be observed with suspended catalysts, such as, for example, Raney nickel.

Hydrogenation processes may be characterized by the conversions, selectivities, and space-time yields achievable therewith. Conversion indicates the number of moles of educt (in this case 3-hydroxypropionaldehyde) that are converted into other substances by hydrogenation. Conversion is usually stated as a percentage of the introduced moles of educt:

$$\text{Conversion of } HPA\ (\%) = \frac{\text{mols of } HPA \text{ converted}}{\text{mols of } HPA \text{ supplied}} \times 100$$

In contrast, selectivity of the hydrogenation process is a measure of the number of moles of converted educt which are converted into the desired product:

$$\text{Selectivity } (\%) = \frac{\text{mols of 1,3-propanediol}}{\text{mols of } HPA \text{ converted}} \times 100$$

The space-time yield is another important characteristic for continuous hydrogenation processes, stating the achievable quantity of product per unit time and reaction volume.

When hydrogenating 3-hydroxypropionaldehyde to 1,3-propanediol on a large industrial scale, it is vital, with regard to the economic viability of the hydrogenation process and the quality of the product, for conversion and selectivity to be as close as possible to 100%. The 1,3-propanediol may be separated from the water as well as remaining 3-hydroxypropionaldehyde and secondary products contained in the product stream by distillation after the hydrogenation. However, this distillative separation is rendered very difficult by residual 3-hydroxypropionaldehyde and secondary products and may even become impossible due to reactions between the residual 3-hydroxypropionaldehyde and 1,3-propanediol to yield acetals, which have a boiling point close to the boiling point of 1,3-propanediol. Thus, the lower the conversion and selectivity, the poorer the achievable product quality.

In order to produce 1,3-propanediol economically, it is also important for the catalyst to exhibit high activity for the hydrogenation of 3-hydroxypropionaldehyde. The objective should thus be to find a process in which the smallest possible quantity of catalyst is necessary for the production of 1,3-propanediol; i.e., it should be possible to achieve the greatest possible conversion of 3-hydroxypropionaldehyde to 1,3-propanediol with a small volume of catalyst.

Conversion, selectivity, and space-time yield are influenced by the characteristics of the catalyst and by the hydrogenation conditions, such as reaction temperature, hydrogen pressure and duration of hydrogenation or, in the case of continuous hydrogenation, by the liquid hourly space velocity (LHSV).

When hydrogenating 3-hydroxypropionaldehyde to 1,3-propanediol, it should be noted that the main reaction is linearly dependent upon hydrogen pressure and time (space velocity in continuous processes), while reaction temperature has scarcely any influence. In contrast, the formation of secondary products is exponentially dependent upon temperature. Under otherwise identical conditions, secondary product formation may be observed to double per 10° C., which correspondingly reduces the selectivity. Increasing the hydrogen pressure, in contrast, has a positive effect on selectivity, although the positive effect of pressure on selectivity is less pronounced than the negative effect of an increase in temperature, as hydrogen pressure increases the rate of the main reaction only linearly, while an increase in temperature increases the rate of the secondary reactions exponentially.

One important quality criterion for the catalysts used in the hydrogenation process is their operational service life. Good catalysts should ensure constant conversion and selectivity in the hydrogenation of 3-hydroxypropionaldehyde to 1,3-propanediol over the course of their service life. Known prior art hydrogenation processes, in particular those based on nickel catalysts, exhibit inadequate long-term stability in this connection. This entails more frequent replacement of the entire catalyst packing, which is associated with known problems in the disposal and working up of compounds containing nickel.

It is known from the 1991 Engelhard brochure *Exceptional Technologies* to hydrogenate aliphatic carbonyl compounds to the corresponding alcohols in the presence of ruthenium on aluminum oxide (Escalit).

It is known from the Degussa brochure *Powder Precious Metal Catalysts* (published 6/95) to hydrogenate aliphatic aldehydes to alcohols in the presence of supported ruthenium catalysts. Aluminum oxide is stated as the support in this case.

Arntz et al. European Patent EP-B 535 565 discloses a process for the production of 1,3-propanediol by heterogeneously catalyzed hydrogenation of 3-hydroxypropionaldehyde in an aqueous solution, in which the supported catalyst consists of titanium dioxide on which finely divided platinum is present in a quantity of 0.1 to 5 wt. % relative to the support. This process has the disadvantage that a relatively high hydrogenation pressure is required to provide substantially constant and high conversion over the service life of the catalyst. Moreover, due to its low activity, a relatively large quantity of platinum catalyst is required in order to achieve a sufficiently high level of conversion. Due to the high price of platinum, this correspondingly substantially increases the costs of the hydrogenation process.

SUMMARY OF THE INVENTION

The object of the present invention is accordingly to provide a hydrogenation process which does not exhibit the stated disadvantages of the prior art processes.

The present invention provides a process for the production of 1,3-propanediol by heterogeneously catalyzed hydrogenation of 3-hydroxypropionaldehyde in an aqueous solution at a temperature of 30° to 180° C., a hydrogen pressure of 5 to 300 bar and a pH value of 2.5 to 7.0, which process is characterized in that the catalyst used is a supported catalyst which consists of an oxide phase, preferably an oxide phase which is resistant to an acidic medium, and on which is present ruthenium, preferably in a quantity of 0.1 to 20 wt. %, relative to the oxide phase. Preferred oxide phases suitable as support materials include $TiO_2$ and $SiO_2$.

The process of the current invention provides high constant conversion of 3-hydroxypropionaldehyde to 1,3-propanediol over the service life of the catalyst. The high constant conversions obtained are maintained even at low hydrogen pressures, for example less than 90 bars. On the other hand, prior art catalysts such as $Pt/TiO_2$, are not satisfactory at low hydrogen pressures.

DETAILED DESCRIPTION OF THE INVENTION

The process of the current invention comprises hydrogenation of 3-hydroxypropionaldehyde in the presence of a supported ruthenium catalyst to form 1,3-propanediol, wherein the support comprises an oxide phase. Preferably the ruthenium is present on the support in a finely divided state in a quantity of 0.1 to 20 wt % relative to the oxide phase.

Examples of oxide materials which are suitable for use as the oxide phase include titanium dioxide, $SiO_2$, $Al_2O_3$ and/or the mixed oxides thereof, such as aluminum silicate. Other suitable oxide phases include MgO, zeolites and/or zirconium dioxide. Such substances are described, for example, in *Catalyst Supports and Supported Catalysts* by Alvin, B., Stiles Verlag, Butterworths 1987, Chapters 2 and 3. It is also possible to use mixtures of oxide phases as the support material.

An oxide phase which is resistant to an acidic medium is preferably used. Such oxide phases include substances selected from the group including titanium dioxide, $SiO_2$ and/or the mixed oxides thereof, such as aluminum silicate. Zeolites and/or zirconium dioxide are also resistant to acidic media. Aluminum oxide and magnesium oxide have lower acid resistance.

In a preferred embodiment of the invention, oxides of titanium and/or silicon and mixed oxides of titanium, silicon and aluminum are used as the oxide phase.

The titanium dioxide used may be a pyrogenically produced titanium dioxide, particularly titanium dioxide produced by flame hydrolysis. The pyrogenic titanium dioxide used may, for example, be obtained from titanium tetrachloride by flame hydrolysis and having a BET surface area of 40 to 60 $m^2/g$ and a total pore volume of 0.25 to 0.75 ml/g, an average primary particle size of 20 nm, a density of 3.7 $g/cm^3$ and an X-ray structure of 20 to 40% rutile and 80 to 60% anatase and is contaminated with less than 0.5 wt. % of silicon dioxide, aluminum oxide, and iron oxide. Pyrogenic titanium oxide, such as the material P25 from Degussa, is particularly suitable as a support for the catalytically active component, and has an elevated BET specific surface area of on average 50 $m^2/g$ (measured according to DIN 66131).

The oxides may be shaped into moldings such as, for example, pellets, granules, or extrudates using methods known in the art, such as those described in Arntz et al. U.S. Pat. No. 5,364,984.

The oxide phase may be coated by means of the Incipient Wetness Method, published in *Preparation of Catalyst,* Delmon, B., Jacobs, P. A., Poncald, G. (eds.), Amsterdam Elsevier, 1976, Page 13. To this end, the water absorption capacity of the support is determined. An aqueous ruthenium chloride solution is prepared which has a concentration corresponding to the subsequent ruthenium coating. The support is loaded with the aqueous ruthenium chloride solution in accordance with its water absorption capacity such that the entire quantity of the solution is absorbed. The loaded support is then dried, preferably at 20° to 100° C. at atmospheric pressure in an inert gas atmosphere, such as neon, helium, argon, nitrogen or air. The drying step may also be conducted under pressure or vacuum. The dried impregnated support is then reduced with hydrogen to form metallic ruthenium, preferably at a temperature of 100° to 500° C. for a period of 20 minutes to 24 hours, generally at atmospheric pressure and a hydrogen concentration of 1 to 100% as a mixture with nitrogen. The reduced catalyst is then optionally washed until free of chloride, preferably to <100 ppm Cl. This preparation provides a fine subdivision of the ruthenium on the catalyst carrier, with crystallite sizes generally between 1 and 5 nm as measured by transmission electron microscopy. The ruthenium is disposed on the support in a quantity of from 0.1 to 20 wt %, preferably about 0.1 to 10 wt %, most preferably about 0.5 to 5 wt % relative to the weight of the oxide phase.

The 3-hydroxypropionaldehyde is reacted with hydrogen in the presence of the supported ruthenium catalyst using methods known in the art. For example, stirred reactors or flow reactors may be used. A fixed-bed hydrogenation reactor is particularly suitable for conducting the hydrogenation on an industrial scale. In such a reactor, the liquid reaction mixture flows or trickles over the fixed-bed catalyst together with the hydrogen introduced. To ensure good distribution of the hydrogen in the reaction mixture and uniform distribution of the gas/liquid mixture over the entire cross-section of the fixed bed, the liquid reaction mixture and hydrogen may be passed together through static mixers before the catalyst bed. Trickle bed reactors are particularly preferred and are described in Kirk-Othmer Encyclopedia of Chemical Technology, Third Edition, Volume 19, pages 880–914 (especially page 884). A trickle bed reactor is preferred because it provides low liquid hold-up time, thus reducing the extent of side reactions such as acrolein formation from 3-hydroxypropionaldehyde resulting in a higher selectivity.

The 3-hydroxypropionaldehyde is generally fed to the reactor as an aqueous solution having a 3-hydroxypropionaldehyde concentration of between 2 and 20 wt % and a pH between 2.5 and 7.0. In continuous processes, liquid hourly space velocities between 0.1 and 10 $h^{-1}$ are preferred. The hydrogenation reaction is conducted at a temperature of from 30° C. to 180° C. at a hydrogen pressure of 5 to 300 bar, preferably at a hydrogen pressure of less than 90 bar, most preferably from 10 bars to 60 bars. It is an advantage of the current invention that high constant conversions are obtained at lower hydrogen pressures compared to other catalysts. For example, the titanium dioxide supported platinum catalysts of Arntz et al. U.S. Pat. No. 5,364,984 generally require hydrogen pressures greater than about 90 bars to achieve high and constant conversion over the service life of the catalyst.

EXAMPLES

The catalysts were tested under steady-state conditions in order to ascertain long-term performance. Hydrogenation was performed continuously in a trickle bed apparatus (Kirk-Othmer Encyclopedia of Chemical Technology, Third Edition, Volume 19, pages 880–914 (especially page 884) having a reactor volume of 140 ml. The apparatus consisted of a liquid vessel, the fixed bed reactor, and a liquid separator. The reaction temperature was adjusted by means of a heat transfer medium/oil circuit. The pressure and hydrogen stream were electronically controlled. The aqueous 3-hydroxypropionaldehyde solution was apportioned to the hydrogen stream with a pump and the mixture introduced into the top of the reactor (trickle bed operation). Once the mixture had passed through the reactor, the resultant product was removed from the separator at regular intervals. In every case, 50 ml of catalyst was used and the 3-hydroxypropionaldehyde concentration in the educt solution was 10 wt. %, with the pH of the educt about 4.0. The hydrogenation temperature was 40° C., the hydrogen pressure 40 bar, and the liquid loading, LHSV, was 1.0 $h^{-1}$. Table 1 summarizes the results of the tests according to various examples. The residual 3-hydroxypropionaldehyde concentration in The reaction product was measured by GC and used in calculating the reported conversions. In all examples, the selectivity was greater than 98% (1,3-propanediol concentration measured by gas chromatography).

The catalysts were prepared according to the following method:

1. The water absorption of the support was determined in g of $H_2O$ per 100 g of support.

2. $RuCl_3$ was dissolved in distilled water for loading 250 ml of support (see Table 1).

3. 250 ml of support were introduced into a coating pan and the $RuCl_3$ solution was poured over the support while the pan was rotating.

4. The coated support was dried for 16 hours in air at room temperature and then heated to 200° C. in air in a tube furnace.

5. The catalyst was then reduced with hydrogen at 200° C. for 8 hours followed by cooling in hydrogen until the catalyst reached room temperature.

6. The reduced catalyst was washed until free of chloride with three 40 ml portions of distilled water.

| | |
|---|---|
| Support 1: | Silica gel from Grace (0.8–1.2 mm) |
| Name: | V432 |
| Support 2: | Activated carbon from Norit (diameter 2.3 mm) |
| Name: | Norit CNR 115 (olive stones) |
| Support 3: | Activated carbon from Norit (diameter 0.8 mm) |
| Name: | Norit ROX (peat carbon) |
| Support 4: | Titanium dioxide P25 produced pyrogenically by flame hydrolysis from Degussa AG. The support was tempered (950° C. for 12 hrs) and extrusion formed as described in EP 535 565. |
| Support 5: | $Al_2O_3$ from Rhone-Poulenc (diameter 1.1–1.3 mm) |
| Name: | Spheralite 521 |

The following conditions are maintained during coating of the supports:

TABLE 1

| | Support | Water Absorption (g/100 g of Support) | Support (g) | $RuCl_3$ (g) | Water (g) |
|---|---|---|---|---|---|
| Support 1 | $SiO_2$ V432 | 126 | 115 | 11.8 | 145 |
| Support 2 | Norit 1 Extra | 67 | 105 | 10.8 | 56 |
| Support 3 | Norit ROX 0.8 | 80 | 107 | 11.1 | 68 |
| Support 4 | $TiO_2$ EP 0 535 565 | 25 | 100 | 10.2 | 14 |
| Support 5 | $Al_2O_3$ | 74 | 100 | 22.8 | 52 |

TABLE 2

| No. | Catalyst | Support | Operating Time (h) | Conversion (%) |
|---|---|---|---|---|
| VB 1 | 2% pt/$TiO_2$ | according to EP 0 535 565* | 20 | 60 |
| VB 2 | 2% Pt/$TiO_2$ | according to EP 0 535 565* | 300 | 45 |
| VB 3 | 5% Ru/activated carbon | Support 2 | 26 | 71 |
| VB 4 | 5% RU/activated carbon | Support 2 | 216 | 47 |
| VB 5 | 5% RU/activated carbon | Support 3 | 24 | 99.7 |
| VB 6 | 5% Ru/activated carbon | Support 3 | 96 | 60 |
| B 1 | 5% Ru/$TiO_2$ | Support 4 | 19 | 84 |
| B 2 | 5% Ru/$TiO_2$ | Support 4 | 233.5 | 84 |
| B 3 | 5% Ru/$SiO_2$ | Support 1 | 48 | 90 |
| B 4 | 5% Ru/$SiO_2$ | Support 1 | 434 | 89 |
| B 5 | 10% RU/$Al_2O_3$ | Support 5 | 72 | 79 |
| B 6 | 10% Ru/$Al_2O_3$ | Support 5 | 240 | 77 |

*The P25 $TiO_2$ was tempered (950° C. for 12 hrs) and extrusion formed

Comparison of the results for Comparative Examples VB 1 and VB 2 to the results for the Examples according to the invention, B 1 to B 6, shows that the ruthenium catalysts according to the invention are distinguished by higher activity, i.e., higher conversion compared to the Pt/$TiO_2$ catalysts of the prior art. Comparative Examples VB 1 to VB 6 show that both the platinum on titanium dioxide support and the ruthenium catalysts on activated carbon supports exhibit poor long-term behavior. Both groups of catalysts were deactivated after only a few hundred hours. Although the Ru/activated carbon support used in comparative Examples VB 5 and VB 6 has high initial activity (conversion after 24 h operating time of 99.7%), the conversion decreased by almost 40% over an additional operating time of 72 hours. When the Pt/TiO$_2$ catalyst was used, the conversion decreased by about 25% after 300 hours operating time compared to the conversion after 20 hours operating time. In contrast, the ruthenium catalysts on oxide supports, according to the invention, surprisingly exhibit no tendency to become deactivated. The conversion remains substantially constant for the examples of the invention using oxide-supported ruthenium catalysts over an operating time of about 200–400 hours. The greatest reduction in conversion observed for the examples of the invention was with the Ru/Al$_2$O$_3$ catalyst, for which the conversion was lowered only by about 2.5% after an operating time of about 240 hours compared to the conversion at 72 hours. Ruthenium on SiO$_2$ and TiO$_2$ (Examples B 1 to B 4) in particular exhibit very high activity, the activity remaining substantially constant over an operating time of greater than 200 hours.

While the invention has been described above with respect to certain embodiments thereof, it will be appreciated that variations and modifications may be made without departing from the spirit and scope of the invention.

What is claimed is:

1. A process for the production of 1,3-propanediol comprising:

hydrogenating an aqueous solution of 3-hydroxypropionaldehyde in the presence of a heterogeneous catalyst, the hydrogenating being carried out at a temperature of from 30° C. to 180° C., a hydrogen pressure of 5 to 300 bar and a pH of from 2.5 to 7.0, wherein the catalyst is a supported catalyst comprising an oxide phase on which ruthenium is disposed in a quantity of from 0.1 to 20 wt %, relative to the oxide phase.

2. The process of claim 1, wherein the oxide phase comprises at least one member selected from the group consisting of TiO$_2$, SiO$_2$, Al$_2$O$_3$, MgO, zeolites, zirconium dioxide, and mixed oxides, said mixed oxides comprising at least two members selected from the group consisting of TiO$_2$, SiO$_2$, and Al$_2$O$_3$.

3. The process of claim 2 wherein the oxide phase comprises at least one member selected from the group consisting of TiO$_2$, SiO$_2$, aluminum silicate, zeolites, and zirconium dioxide.

4. The process of claims 2 or 3, wherein the finely divided ruthenium is disposed on the oxide phase in a quantity of from 0.1 to 10 wt %.

5. The process of claims 2 or 3, wherein the finely divided ruthenium is disposed on the oxide phase in a quantity of from 0.5 to 5 wt %.

6. The process of claim 5, wherein the oxide phase is impregnated with ruthenium, using an aqueous solution of a ruthenium compound, and is then reduced in a stream of hydrogen for a period of from 20 minutes to 24 hours at temperatures of from 100° C. to 50° C.

7. The process of claim 1 wherein the hydrogenating step is carried out at a hydrogen pressure of less than 90 bars.

8. The process of claim 7 wherein the hydrogenating step is carried out at a hydrogen pressure of from 10 bars to 60 bars.

9. The process of claims 7 or 8 wherein the oxide phase comprises at least one member selected from the group consisting of SiO$_2$ and TiO$_2$.

10. The process of claim 9 wherein the hydrogenating step is carried out in a trickle bed reactor.

* * * * *

UNITED STATES PATENT AND TRADEMARK OFFICE
CERTIFICATE OF CORRECTION

PATENT NO. : 6,232,511 B1
DATED : May 15, 2001
INVENTOR(S) : Haas et al.

It is certified that error appears in the above-identified patent and that said Letters Patent is hereby corrected as shown below:

Column 8,
Line 25, change "50° C" to -- 500° C --.

Signed and Sealed this

Fourteenth Day of May, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,232,511 B1
DATED : May 15, 2001
INVENTOR(S) : Haas et al.

It is certified that error appears in the above-identified patent and that said Letters Patent is hereby corrected as shown below:

<u>Title page,</u>
Item [57], ABSTRACT,
Line 4, change "at a hydrogenation" to -- a hydrogen --.

Signed and Sealed this

Sixth Day of May, 2003

JAMES E. ROGAN
*Director of the United States Patent and Trademark Office*